US009662182B2

(12) United States Patent
Williams

(10) Patent No.: US 9,662,182 B2
(45) Date of Patent: May 30, 2017

(54) DENTAL SPLINT DEVICE AND METHODS FOR MAKING AND USING SAME

(76) Inventor: Thomas Williams, Sparkill, NY (US)

( * ) Notice: Subject to any disclaimer, the term of this patent is extended or adjusted under 35 U.S.C. 154(b) by 663 days.

(21) Appl. No.: 13/196,686

(22) Filed: Aug. 2, 2011

(65) Prior Publication Data

US 2012/0028221 A1 Feb. 2, 2012

Related U.S. Application Data

(60) Provisional application No. 61/400,784, filed on Aug. 2, 2010.

(51) Int. Cl.
*A61C 5/00* (2017.01)
*A61C 7/00* (2006.01)

(52) U.S. Cl.
CPC ........... *A61C 7/00* (2013.01); *A61C 5/007* (2013.01)

(58) Field of Classification Search
CPC .................................. A61C 7/00; A61C 5/007
USPC .................................. 433/215, 9, 6, 180–181
See application file for complete search history.

(56) References Cited

U.S. PATENT DOCUMENTS

| | | | |
|---|---|---|---|
| 3,395,455 A * | 8/1968 | Overby et al. ............... 433/215 |
| 4,384,854 A | 5/1983 | Garfinkel |
| 4,412,818 A | 11/1983 | Thomson |
| 4,419,992 A * | 12/1983 | Chorbajian .................. 128/862 |
| 4,433,960 A | 2/1984 | Garito et al. |
| 4,504,229 A | 3/1985 | Garito et al. |
| 4,533,320 A | 8/1985 | Piekarsky |
| 4,735,571 A | 4/1988 | Salvo |
| 5,039,303 A | 8/1991 | Irwin |
| 5,087,202 A | 2/1992 | Krenkel |
| 5,120,224 A * | 6/1992 | Golub ........................... 433/215 |
| 5,184,955 A | 2/1993 | Baer et al. |
| 5,360,482 A * | 11/1994 | Belvedere ..................... 118/404 |
| 5,964,589 A * | 10/1999 | Musich ........................... 433/20 |
| 6,257,884 B1 | 7/2001 | Chang |
| 6,648,645 B1 * | 11/2003 | MacDougald et al. ....... 433/223 |
| 6,671,539 B2 | 12/2003 | Gateno et al. |
| 6,916,178 B2 * | 7/2005 | Lans .............................. 433/181 |

(Continued)

OTHER PUBLICATIONS

Sirona, CEREC Connect Product Sheet, http://www.sirona.com/ecomaXL/index.php?site=SIRONA_COM_digital_impression_cerec_connect Visited Aug. 2, 2011 (two pages).

(Continued)

*Primary Examiner* — Heidi M Eide
(74) *Attorney, Agent, or Firm* — John F. Vodopia

(57) ABSTRACT

Disclosed is a method of fabricating a dental splint for stabilizing mobile or unstable teeth or firmly rooted teeth to prevent orthodontic relapse. The fabricating of the dental splint includes the steps of: a patient's dental arch to determine if lingual reduction is required, creating a representative model of the patient's dental arch, manipulating the representative model to select a group of teeth to be included in the dental splint and to define the height and length of a one-piece extracoronal component customized to the dentition of a patient; fabricating the one-piece extracoronal component, dry fitting the fabricated one-piece extracoronal component to confirm proper fit, and adhering the fabricated one-piece extracoronal component to the mobile or unstable teeth, wherein the one-piece extracoronal component adheres to the lingual aspect of the teeth and appears substantially non-visible facially.

12 Claims, 6 Drawing Sheets

(56) References Cited

U.S. PATENT DOCUMENTS

| | | |
|---|---|---|
| 7,048,542 B2 | 5/2006 | Von Arx et al. |
| 2006/0078849 A1 | 4/2006 | Parks |
| 2008/0090207 A1* | 4/2008 | Rubbert .................. 433/171 |
| 2010/0104998 A1 | 4/2010 | Farrell et al. |

OTHER PUBLICATIONS

Sirona, inLab MC XL Product Sheet, http://www.sirona.com/ecomaXL/index.php?site=SIRONA_COM_inlab_system_hardware_inlab_mcxl Visited Aug. 2, 2011 (one page).

Sirona, inLab 3D Product Sheet, http://www.sirona.com/ecomaXL/index.php?site=SIRONA_COM_inlab_system_software# Visited Aug. 2, 2011 (one page).

* cited by examiner

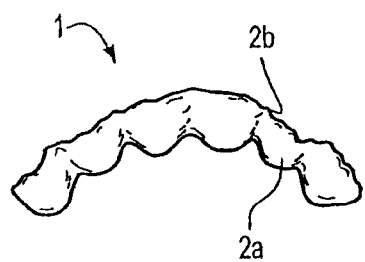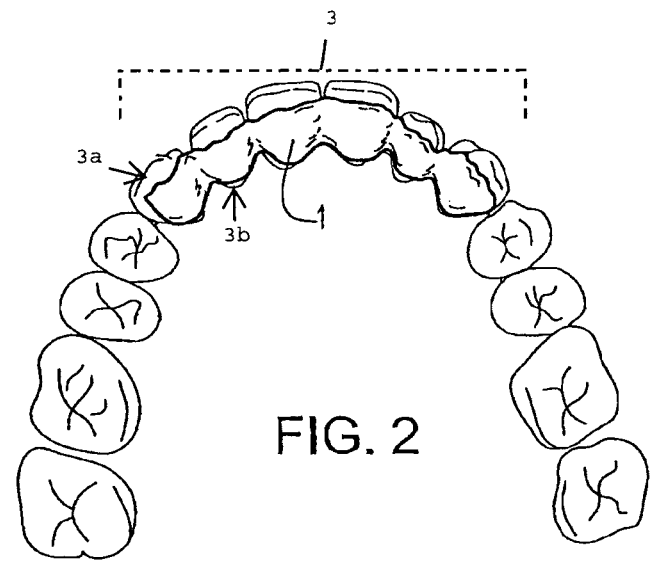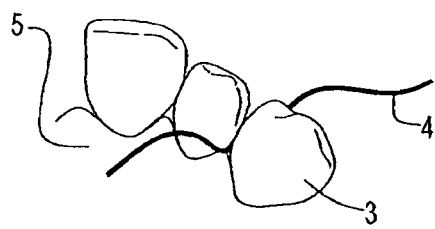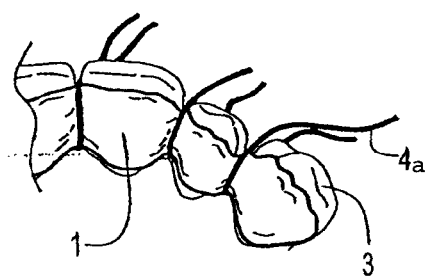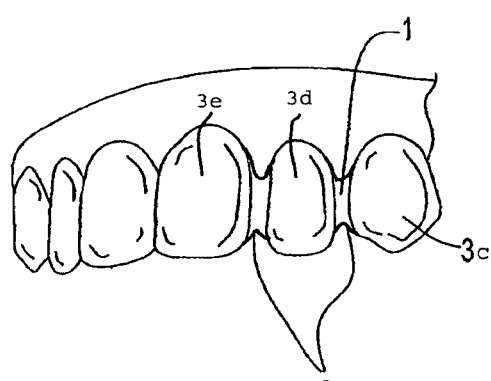
FIG. 1
FIG. 2
FIG. 3
FIG. 4
FIG. 5

CLINICAL INSERTION OF THE SPLINT
(CONT.)   Ⓐ

GENTLE BUT FIRM PRESSURE IS APPLIED TO THE LOOPED DENTAL FLOSS FROM A FACIAL DIRECTION TO PULL THE SPLINT AGAINST THE LINGUAL SURFACE OF THE TEETH, THEREBY INSURING AN INTIMATE FIT AND MINIMIZING THE THICKNESS OF THE RESIN CEMENT — 190

WHILE APPLYING CONSISTENT PRESSURE WITH THE DENTAL FLOSS LOOPS FROM A FACIAL DIRECTION, EXCESS RESIN CEMENT CAN BE REMOVED WITH Q-TIP APPLICATORS, BONDING BRUSHES OR ANY OTHER INSTRUMENTS OF CHOICE — 200

IF USING A LIGHT-CURED RESIN CEMENT, THE CURING LIGHT MAY BE APPLIED TO INITIATE HARDENING OF THE RESIN CEMENT. IF USING A SELF-CURED RESIN CEMENT, PRESSURE WITH THE FLOSS SHOULD BE MAINTAINED UNTIL RESIN CURING IS COMPLETE — 210

INTRA-ORAL EVALUATION IS THEN PERFORMED AND ANY RESIDUAL CEMENT IS REMOVED FROM THE TOOTH OR TEETH INVOLVED AS WELL AS THE GUM TISSUE AREAS — 220

REMOVAL OF THE INCISALLY-PLACED END OF THE DENTAL FLOSS WILL PERMIT FLOSSING BENEATH THE SPLINT AND ASSIST IN REMOVING ANY GINGIVAL EXCESS CEMENT — 230

THE OCCLUSION IS EVALUATED AND THE BITE IS ADJUSTED ACCORDINGLY USING DIAMOND GRIT INSTRUMENTS UNDER A COPIOUS WATER SPRAY — 240

SPLINT MAINTENANCE AND HYGIENE PROCEDURES (SUCH AS USE OF FLOSS THREADERS) ARE THEN DISCUSSED WITH THE PATIENT AS ARE ARRANGEMENTS FOR ROUTINE PERIODIC EVALUATION OF THE SPLINT — 250

FIG. 6D

DENTAL SPLINT DEVICE AND METHODS FOR MAKING AND USING SAME

CROSS-REFERENCE TO RELATED APPLICATIONS

This United States Non-Provisional Patent Application claims priority to and the benefit of U.S. Provisional Application No. 61/400,784, filed Aug. 2, 2010 and entitled "Dental Splint Device and Methods for Making and Using Same," said provisional application is hereby incorporated herein in its entirety.

BACKGROUND OF THE INVENTION

1. Field of the Invention

The present invention relates a dental splint for stabilizing mobile or unstable human or animal teeth or firmly rooted teeth and more, particularly an apparatus and method for fabricating such a splint and the procedure for installing same.

2. Description of the Related Art

Stabilizing dental retainers and/or dental splints have been used in dentistry and orthodontics for many years to maintain natural teeth in a desired position. For example, it often is necessary to immobilize (and/or support) teeth which have been re-positioned orthodontically (especially when that orthodontic treatment has resulted in a condition called "root blunting" or "root resorption"), or teeth which exhibit a loss of bone support as result of periodontal disease. Stabilization also may be indicated in circumstances resulting from traumatic injury. As a general proposition, stabilization of teeth through use of a dental splint often involves connecting the teeth to be supported to one or more teeth that are firmly anchored in the mouth.

Historically, a number of different removable facial and lingual devices have been employed to stabilize teeth. The well-known Hawley Retainer is often employed with respect to maxillary and or mandibular anterior teeth. That type of retainer uses a metal wire positioned on the facial surface of teeth connected to an embeddable acrylic on the lingual aspect of the subject teeth to aid in retention of the appliance. Additional attempts have involved bonding various components to the lingual aspect on the anterior teeth and imbedding a metal wire within a bonded bracket or within the bonded material itself. The actual thickness of these bonded components frequently result in accessibility concerns for hygiene maintenance as well as plaque and calculus retention which can contribute to both periodontal as well as restorative concerns (i.e., cavities). Other approaches for the stabilization of teeth have employed a metal wire which is custom adapted to a groove or channel that has been cut into the enamel (or into the dentin) on the lingual aspect of the teeth. The wire is then fitted into the channel and overlaid with composite and bonded into place. Although this process reduces hygienic concerns, it involves removal of sound tooth structure and consequently is not reversible. Still other methods have involved the use of extracoronal dental splints fabricated from metal or other malleable strips of materials that are attached to the inner dental arch with composite or other bonding materials. Typical examples of removable facial and lingual devices found in the prior art are described below.

U.S. Pat. Appln. No. 2010/0104998 entitled "Dental Splint" and applied for by Farrell et al. discloses a "removable" occlusal dental splint for treatment of certain orofacial disorders and includes a chewing surface where the splint can be employed while eating. The specification describes the one or more clasps fitted to the splint for adjusting the fit of the splint and to help retain the appliance in the mouth.

U.S. Pat. No. 4,412,818 entitled "Method for Splinting Animal Teeth," and issued to Thomson discloses a simple method of stabilizing grazing animal's teeth (all of them) where an aperture brace (single elongated strip) is bonded to the teeth by means of a bonding composition leaving the incisal edges of the teeth exposed.

U.S. Pat. No. 4,735,571 entitled "Dental Splint" and issued to Salvo discloses a dental splint procedure comprising the steps of providing a rigid bar member; forming a dental preparation in the surface (only so deep as into the dentin) of a plurality of teeth providing a filled resin composite material and bonding agent to adhere the bar; coating the walls and floor of the bar; coating the floor and walls of the dental preparation; mounting the bar into the preparation; and covering the bar and preparation so as to form a unitary structure.

U.S. Pat No. 4,433,960, entitled "Extracoronal Dental Splint and Splinting Method," issued to Garito discloses a dental splint and dental splint procedure which utilizes a thin, flat, slightly malleable perforated strip or mesh (grid-like material) which is adhered to the patient's inner dental arch employing a pressure-sensitive adhesive backing. Garito's dental splint is actually two strip segments with a hinge connecting together the two similar segments at their adjacent ends by way of a pin. Subsequently, the two strip segment is covered with a thin layer of resin or composite material, which when hardened firmly bonds the strip to the patient's teeth (i.e. to stabilizing any mobile teeth).

U.S. Pat No. 4,504,229 entitled "Dental Placement Device and Method," issued to Garito et al discloses a dental placement device and related method for placement of dental splints for stabilizing mobile or avulsed teeth. In particular, the procedure includes the steps of (a) bonding a malleable mesh-type elongated strip onto and over the occlusial surface of the tooth; (b) trimming off excess strip sections extending beyond the occlusial surface; and (c) adjusting the exposed bonded strip to enhance its biting function. The dental placement procedure includes the steps of inserting monofilaments which are joined at opposite ends by common joining strips (interproximally into a segment of teeth); (b) placing splinting material across the teeth and in the interproximal spaces; (c) looping the monofilaments over the splinting material and back into the interproximal spaces and pulling same so as to draw the splinting material into the said interproximal spaces; and (d) applying a hardenable bonding material over the splinting material while temporarily held by the monofilaments and allowing the bonding material to harden. The monofilaments are also employed to draw splinting material into interproximal spaces during the procedure.

U.S. Pat. No. 4,384,854 entitled "Anterior Splint," and issued to Garfinkel discloses an anterior splint including an elongated anchoring member (i.e., "tab") and wire mesh strip coupled to the anchoring member wherein the wire mesh strip is engaged to the lingual surface of the teeth and forced into the interproximal spaces. In other words, Garfinkel's dental splint requires that the dentist pull labially on the tab which forces the wire mesh into the interproximal spaces against the lingual surfaces. Subsequently, the wire mesh and tabs are bonded to the teeth lingually and interproximally (with excess removed). An optional step is disclose of stripping a thin ledge on the anterior teeth (interproximally) to provide more facility in the inserting of tabs.

U.S. Pat. No. 6,916,178 entitled "Dental Splint and Splinting Method," and issued to Lans discloses a splint and method for installing same on adjacent teeth. The splint is formed of a rigid sheet material (stainless steel or titanium 0.0007 inches thick) and has two support prongs extending in opposite direction to each other from two shoulders that are connected by an arch portion that extends between the shoulders. The method includes installing aligned grooves cut into adjacent teeth using a simple inverted core carbide bur. The grooves are partially filled with composite resin, after which the splint is embedded in the composite resin, which is then cured and finished to a smooth surface.

U.S. Pat. No. 7,048,542 entitled "Dental Splint," and issued to Arx, discloses a dental splint for fixing a tooth with increased mobility. This splint has a plurality of eyes, wherein adjacent eyes interconnected via a flat connection and individual eyes, each have a through-opening which is surrounded by a link so that it is possible (by way of the through-opening) to apply an adhesive to the tooth located behind the respective through-opening to secure the dental splint on the tooth. Each eye is substantially diamond-shaped with a flat connection between the eye at least approximately twice as wide as the link which surrounds the through-openings.

U.S. Pat. No. 5,184,955 entitled "Device for Temporary Dental Splinting," and issued to Baer et al. discloses a device and a related method for temporary fixation of teeth comprising a wire-shaped connecting link and a row of annular composite carriers wherein composite material is applied to each tooth surface. The invention further includes an embodiment where the annular composite carriers have two sides which lie substantially opposite of one another, including a hole for the connecting link. Moreover, the device can be enhanced through ergonomic principles such as a "skull-capped" configuration with openings to receive the wire-shaped connecting link.

U.S. Pat. No. 4,533,320 entitled "Stabilizing Retainer System" and issued to Piekarsky discloses a stabilizing retainer (and similar method of installing same) comprising a conformable wire for placement in a predetermined position and spanning a series of teeth; a plurality of bonding pads for securing the wire to a group of teeth; wherein each said bonding pad further includes a basal surface portion and transverse channel for receiving the wire and securing it to each pad.

U.S. Pat. No. 5,087,202 entitled "Device to Fix or Control the Mutual Position of Teeth," and issued to Krenkel discloses a device to fix and control the mutual position of teeth including a unitary strip of deformable material substantially elongated in a longitudinal direction. Each unitary strip includes a plurality of anchor elements which are connected to one another by a force transfer member (claimed as a "continuous connecting bar" or "connection bars"). The various embodiments of Krenkel each disclose anchor element being substantially ring-like in configuration and the rings exhibit chamfered inner.

U.S. Pat. Appln. No. 2006/0078849 entitled "Dental Splint" and applied for by Parks discloses a dental splint which involves the installation a plurality of splint posts onto one or more teeth and the insertioning/installation of a strip to interconnect the plurality of the splints. One embodiment discloses that each splint post has a ovoidal-shaped top and a rectangular base with each strip including similar ovoidal shaped slots for connecting the strip and the splint posts. Another similar embodiment includes a splint post with a ovoidal base and rectangular top where the base and top are separable (including a notches and slots for securing the two parts). Yet another embodiment provides an additional groove disposed in the top of the splint posts for receiving a wire or band. Similarly, another embodiment discloses a splint post which has the ability to move laterally (90°) within the slot relative to the longitudinal axis of the strip. Moreover, the strip has "snap into" channels for receiving "keys" provided on the bottom of the splint post top. Another embodiment of Parks discloses a domed top splint post which includes a flat base and a domed top. The flat base includes a peel strip that can be removed to expose resin for adhering to the teeth. The domed top includes a passage which includes one or more protrusions that engage one or more ridges on a strip to fasten the splint posts (i.e. zip or cable ties). Another similar embodiment disclosed by Parks utilizes a rectangular top splint post instead of a domed top. Yet another embodiment of Parks discloses silted ("snap" top) splint post which includes a slit to allow a strip to snap into a deeper and wider passage.

The prior art also discloses a method of fabricating dental devices. For example, U.S. Pat. No. 6,671,539 entitled "Method and Apparatus for Fabricating Orthognathic Surgical Splints," and issued to Gateno discloses a method of forming a surgical splint to receive a patient's dentition allowing selective alignment of the upper and lower jaw relative to the patient's skull during surgery comprising the steps of: (a) generating a CT computer model of bone structure; (b) generating a digital dental computer model of patient's dentition; (c) positioning a plurality of markers relative to the patient's dentition in both the CT and digital computer models; (d) forming a composite model of the CT and digital dental model; (e) displaying the composite computer model; (f) forming a planned position computer model (repositioning of upper or lower jaw with respect to patient's skull); (g) forming a computer model surgical splint of patient's dentition; and (h) forming a surgical splint from the computer model surgical splint.

While such dental splints and methods described above offer some advantages over prior methods, they still have some disadvantages when compared to the present invention addressed herein. For example, those disadvantages include: (1) greater time and effort required for their fabrication and installation; (2) a less precise matching of the appliance to the contours of the existing teeth of the inner arch which contributes to hygienic and restorative concerns; (3) greater bulk than the dental splint invention addressed herein; (4) the use of materials that are not as dense, color stable and bio-compatible as those used in the present invention; (5) the need to apply extra composite or bonding material around the edges of the splint; (6) less aesthetically pleasing appearance due to the use of non-tooth-colored material; (7) the need to have the splint span a larger minimum number of teeth (e.g., four teeth) whereas the present invention can be utilized with a minimum of two teeth (i.e., one tooth to be supported attached to one support tooth); (8) the need to use acrylic monomer which may cause allergic reactions or irritations; and (9) the need for one or more stable or firmly-rooted teeth to which to bond the dental splint.

Having set forth the limitations of the prior art, it is clear that what is required is a custom-fabricated lingual extra-coronal dental splint along with the processes for manufacturing and bonding or installing that splint. One objective of the present invention is to produce an ideal splint that should exhibit the following characteristics: (1) it should be made of a tooth colored material, (2) it should be strong and rigid even when manufactured in thin dimensions, (3) it should maintain existing tooth contours without creating bulkiness, (4) it should enhance hygiene maintenance and thereby also decrease restorative concerns, (5) it ordinarily should not require the alteration of existing tooth structure, and (6) it could be removable by a dental professional if the conditions prompting its installation change (for example, in the case of a traumatic injury) or if the patient desires removal of the device.

SUMMARY OF THE INVENTION

In accordance with the present invention, there is provides a dental splint for stabilizing mobile or unstable teeth. More particularly a dental splint comprising a one-piece extracoronal component customized to the dentition of a patient wherein the one-piece extracoronal component is adhered to the lingual aspect of the teeth and substantially non-visible facially.

In one aspect, the invention comprises a one-piece extracoronal component is made from zirconia, alumina (or a material with similar properties).

In one embodiment, the one-piece extracoronal component functions substantially as a force transfer component.

In yet another embodiment, the one-piece extracoronal component is of a consistent thickness of 0.4 mm.

Alternatively, the one-piece extracoronal component is of a thickness of 0.7 mm.

In one embodiment, the one-piece extracoronal component is of a variable thickness in a range from and including 0.3 mm up to and including 1.5 mm, depending upon the location of the dental splint in the mouth and particular purpose or purposes to which the splint would be put. Alternatively, the one-piece extracoronal component is of a consistent thickness in a range from and including 0.3 mm up to and including 1.5 mm, depending upon the location of the dental splint in the mouth and particular purpose or purposes to which the splint would be put.

In yet another aspect, the one-piece extracoronal component is configured to not fully cover each tooth, wherein a portion of the tooth is exposed at the bite edge and above the gingival.

In yet another embodiment, the one-piece extracoronal component is made of zirconia, alumina (or a material with similar properties) and a bonding agent which are color-matched to a patient's teeth.

In still another embodiment the one-piece extracoronal component is installed on a group of two teeth.

Yet another aspect, the invention comprises a one-piece extracoronal component bonded to a group of teeth, wherein said group of teeth have firmly rooted teeth at least at one end of the splint. Alternatively, the one-piece extracoronal component is bonded to a group of teeth, wherein said group of teeth are all mobile or unstable.

In yet another embodiment a method for fabricating a dental splint for stabilizing mobile or unstable teeth is disclosed. More specifically, a fabrication method comprising the steps of: examining patient's dental arch to determine if lingual reduction is required; creating a representative model of the patient's dental arch; manipulating said representative model to select a group of teeth to be included in the dental splint and to define the height and length of a one-piece extracoronal component customized to the dentition of a patient; fabricating said one-piece extracoronal component; dry fitting the fabricated one-piece extracoronal component to confirm proper fit; and adhering the fabricated one-piece extracoronal component to said mobile or unstable teeth, wherein said one-piece extracoronal component adheres to the lingual aspect of said teeth and appears substantially non-visible facially.

In one embodiment, the method step of creating a representative model of the patient's dental arch further includes the steps of: selecting an impression tray appropriate to a patient's mouth; pouring an impression material in said selected impression tray; allowing said impression material to harden in the patient's mouth; and fabricating from plaster or dental stone said representative model.

In one aspect, the step of creating a representative model of the patient's dental arch further includes the steps of: scanning a three dimensional (3D) image of the patient's dental arch with a commercially available scanning device.

In yet another embodiment, the fabrication method a commercially available scanning device further incorporates computer software for generating a virtual model of a patient's dentition.

In still another embodiment, the step of manipulating said representative model to select a group of teeth to be included in the dental splint and to define the height and length of a one-piece extracoronal component customized to the dentition of a patient further includes the steps of: adjusting the distance between the bite edge of each said tooth and the edge of the one-piece extracoronal component 1-4 mm from the bite edge and 1 mm above the gum between the tooth and its adjacent tooth.

Alternatively, the step of fabricating said one-piece extracoronal component further includes the steps of: milling said one-piece extracoronal component with a thickness of 0.4 mm.

In still yet another embodiment the step of fabricating said one-piece extracoronal component further includes the steps of: milling said one-piece extracoronal component with a thickness of 0.7 mm. alternatively, the step of fabricating said one-piece extracoronal component further includes the steps of milling said one-piece extracoronal component with a thickness of a range from and including 0.3 mm up to and including 1.5 m, depending upon the location of the dental splint in the mouth and the particular purpose or purposes to which the dental splint would be put.

Alternatively, the dental splint is configured for milling a consistent thickness or a variable thickness.

In yet another embodiment the step of fabricating said one-piece extracoronal component further includes the step of: selecting zirconia, alumina (or a material with similar properties) as the material to fabricate said one-piece extracoronal component.

Another aspect of the present invention is the one-piece extracoronal component functions substantially as a force transfer component.

In another embodiment of the present invention the sub-step of selecting zirconia, alumina (or a material with similar properties) further includes the step of color matching said selected material to the patient's teeth.

In yet another aspect of the present invention the one-piece extracoronal component is installed on a group of two teeth.

In still yet another embodiment of the present invention a method of clinically installing a dental splint for stabilizing mobile or unstable teeth is disclosed. In particular, the method comprises the steps of: dry-fitting a fabricated one-piece extracoronal component customized to the dentition of a patient to confirm fit and contour; applying a coupling agent to the bonded side the splint, a rescind to the one-piece extracoronal component and bonding agent to adheres to the teeth the splint; applying a looped floss technique to complete a splint connection between said teeth and said one-piece extracoronal component, wherein said one-piece extracoronal component is adhered to the lingual aspect of said teeth and substantially non-visible facially.

In yet another embodiment, one-piece extracoronal component is bonded to a group of teeth which are all mobile or unstable. An alternative embodiment disclosed herein provides a one-piece extracoronal component bonded to a group of firmly rooted teeth to prevent orthodontic relapse.

BRIEF DESCRIPTION OF THE DRAWINGS

The objects, features and advantages of the present invention will become apparent to one skilled in the art, in view of the following detailed description taken in combination with the attached drawings, in which:

FIG. 1 illustrates a dental splint for application to six teeth according to one embodiment of the present invention, FIG. 2 shows the application of the dental splint to six teeth according to one embodiment of the present invention, FIG. 3 shows a piece of dental floss inserted between one of the teeth to which a dental splint will be bonded according to one embodiment of the present invention, FIG. 4 illustrates an intermediate stage of the installation (or bonding process) of the dental splint according to one embodiment of the present invention, FIG. 5 shows a facial view of certain teeth to which an embodiment of the splint has been bonded on their lingual sides according to one embodiment of the present invention, FIG. 6D is the second half of a flow chart containing the steps employed in clinical insertion of the splint to one embodiment of the present invention.

DETAILED DESCRIPTION OF THE INVENTION

Figure 6A:
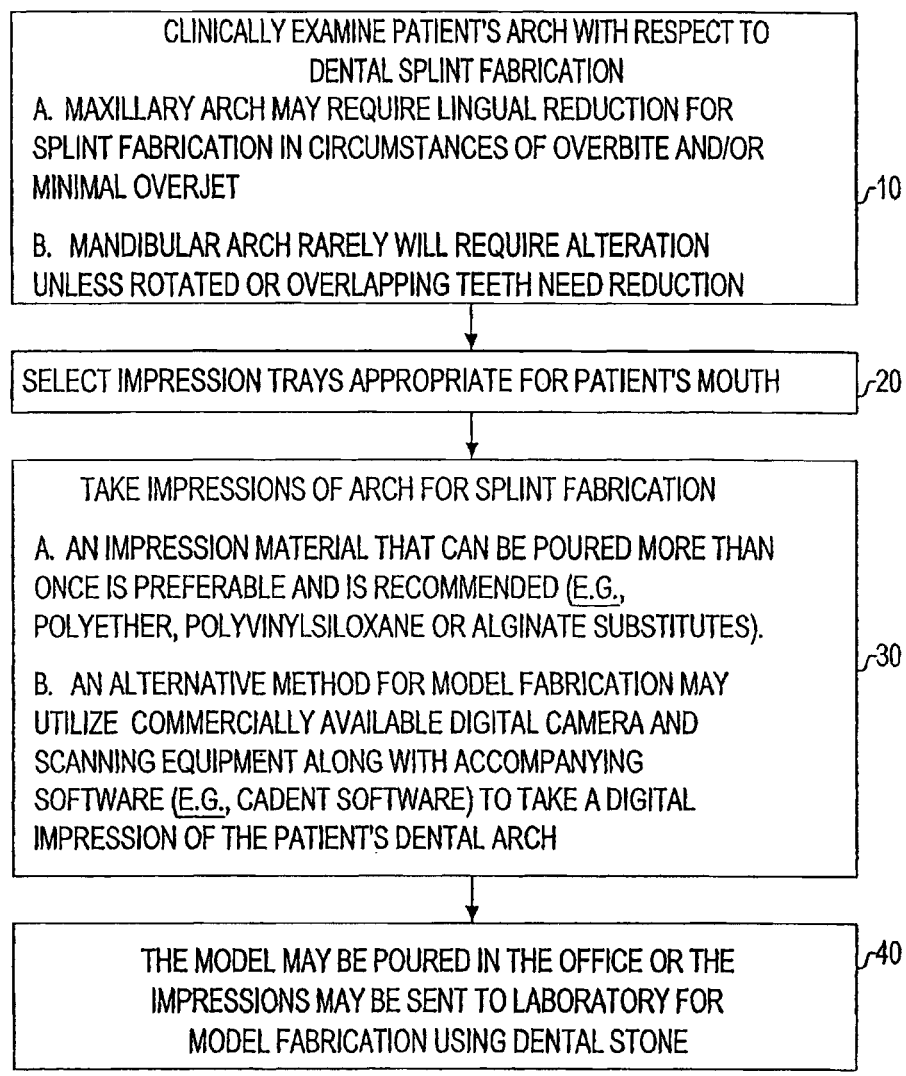
FIG. 6A is a flow chart containing detailed steps of preparing for fabrication of the dental splint according to one embodiment of the present invention.

Hereinafter, embodiments of the present invention will be described with reference to the accompanying drawings. It should be noted that the similar components are designated by similar reference numerals although they are illustrated in different drawings. For the purposes of clarity and simplicity, a detailed description of known functions and configurations incorporated herein will be omitted as it may obscure the subject matter of the present invention.

In accordance with the present invention, there is provided a dental splint device for stabilizing mobile or unstable human or animal teeth, a procedure for fabricating such a dental splint and a dental splinting procedure (i.e., a procedure for installing the splint). Generally speaking, one of the dental splint's basic purposes is the retention of teeth in a desired position in the mouth. More specifically, the device is intended to maintain and/or retain the position of a series of upper or lower teeth within the same arch. The dental splint disclosed herein can be categorized as a permanent or semi-permanent dental appliance in that once installed it can be removed only by a dental professional.

A. Dental Splint

FIG. 1 is an illustration of a dental splint according to one embodiment of the present invention. As shown in FIG. 1, the dental splint 1 is an elongated, flat, one-piece and ridged extra-coronal (that is, external to the natural tooth) and functions substantially as a force transfer component and formed from a model of the dentition of an individual patient's dental arch. The dental splint has two sides; (a) a bonded side 2b which is the mirror opposite of the specific contours of the lingual aspect of each tooth (i.e. lingual fossa, ridges and margins); and (b) a lingual side 2a which is the side exposed to the patient's tongue.

The dental splint shown in FIG. 1 is made of commercially available dental zirconia, or dental alumina (or a material with properties similar to either of those substances). In selecting the material to be used to fabricate a dental splint as described below, factors such as the strength, rigidity, brittleness, durability and its ability to bond to the teeth also should be considered. As stated above, zirconia can be used to produce any dental splint as described herein. Alumina also can be used to produce dental splints described herein. However, since zirconia is a stronger material than alumnia, the former might be the better choice when producing a dental splint for an arch involving a large number of teeth as well as other splints that are expected to be subjected to greater stresses. Yet another embodiment of the present invention provides that the material is of a consistent thickness of 0.4 mm (i.e. maintain existing tooth contours without creating bulkiness). An alternative embodiment provides for a thickness of 0.7 mm. Yet another alternative embodiment provides for a range of thicknesses from and including 0.3 mm up to and including 1.5 mm, depending upon the location of the dental splint in the mouth and the particular purpose or purposes to which the splint would be put.

Since the dental splint described herein is a new invention, clinical data developed through use of various materials to make the splint described herein will undoubtedly provide guidance regarding the best material to use in various circumstances. Furthermore, since new dental materials with different properties and characteristics are always being brought to market, those new materials can be used to fabricate the dental splint described herein if they meet or exceed the desirable characteristics of zirconia or alumina.

Figure 7:
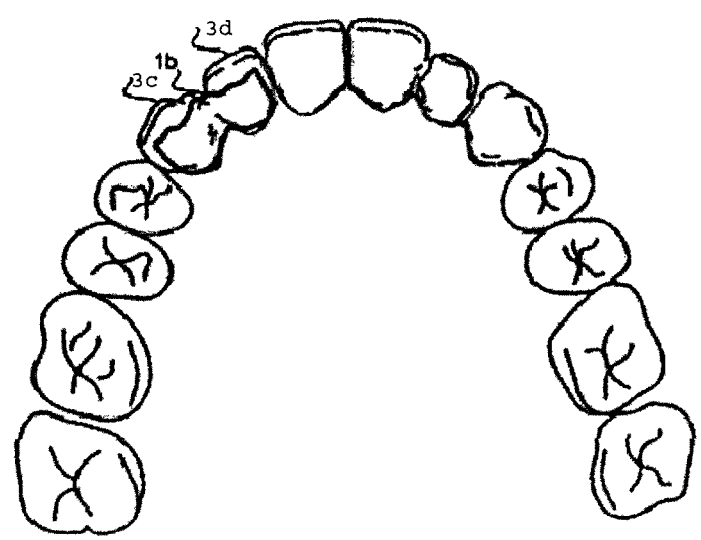
FIG. 7 illustrates a dental splint for application to two teeth according to one embodiment of the present invention.

Referring now to FIG. 2, the application of the above described dental splint 1 to a group of six teeth 3 is shown according to one embodiment of the present invention. As can be seen in FIG. 2, the dental splint 1 does not fully cover each tooth wherein a portion of the tooth is exposed at the bite edge 3a and above the gingival 3b. The specific coverage of the dental splint of a group of mobile or unstable teeth is determined clinically at the outset of the initial consultation with a dental professional while evaluating the patient's bite relationship with the group of teeth (as more fully described below with respect to the fabrication of the dental splint). The selection of the distance of the dental splint to the bite edge prevents subsequent damage to the appliance by the patient. On the other hand, the selection of distance between the appliance and the gingival area enhance hygiene maintenance (i.e., make flossing easier) and thereby also decrease restorative concerns. An alternative embodiment of the present invention is shown in FIG. 7 which is the application of the above described dental splint 1b to two teeth (i.e lateral incisor 3d and cuspid 3c).

Referring now to FIG. 5 a view of certain teeth (i.e. central incisor 3e, lateral incisor 3d and cuspid 3c) shown according to one embodiment of the present invention. More specifically, FIG. 5 illustrates facially the embodiment of the dental splint shown in FIG. 2 which has been bonded to the lingual side of a group of six teeth. As can be seen in FIG. 5, The interproximal spaces 8 (i.e. gaps or horizontal spaces between the bonded teeth) are shown as well as the dental splint 1, which faces the back of the patient's teeth and shows through one of the interproximal spaces 8 (i.e. in an aesthetically pleasing manner). Accordingly, the dental splint appears substantially non-visible facially.

Additionally, the dental splint described in the present invention result in an aesthetically pleasing smile due to the ability to color match the dental splint (and bonding resin) to the patient's teeth. More specifically, and described in more detail below, when selecting the appropriate material (i.e. zirconia), the dental professional must specify the color of the material among the several shades commercially available. Currently, only four shades of zirconia are available. However it is anticipated that number of shades shall increase over time. Color selection generally involves matching the color of the tooth surfaces to which the appliance will be bonded. An alternative embodiment of the present invention provides for color staining of the dental splint as well known in the art.

In order to adhere the present invention's dental splint to a group of teeth; the teeth subjected the "splint connection" (i.e., the teeth to which the splint will be bonded) are etched with phosphoric acid as in traditional bonding procedures as well known in the art. Various commercially-available bonding agents are available which are applied to the tooth side of the dental splint, as well as to the etched or conditioned enamel of the teeth involved in the splint connection. A looped floss technique as known in the art and more thoroughly described below (see FIG. 3-4) is employed to minimize resin thickness. In other words, when adhering the dental splint to the patient's inner dental arch, the dental professional attempts to provide a thin layer of composite or bonding material by pulling the splint tightly to the lingual side of the patient's teeth with the loops of dental floss (as shown is FIG. 4 and described in more detail below). It should be noted that the dental splint of the present invention is removable by a dental professional if the conditions prompting its installation change (for example, in the case of a traumatic injury), or if the patient desires removal of the device.

Figure 6B:
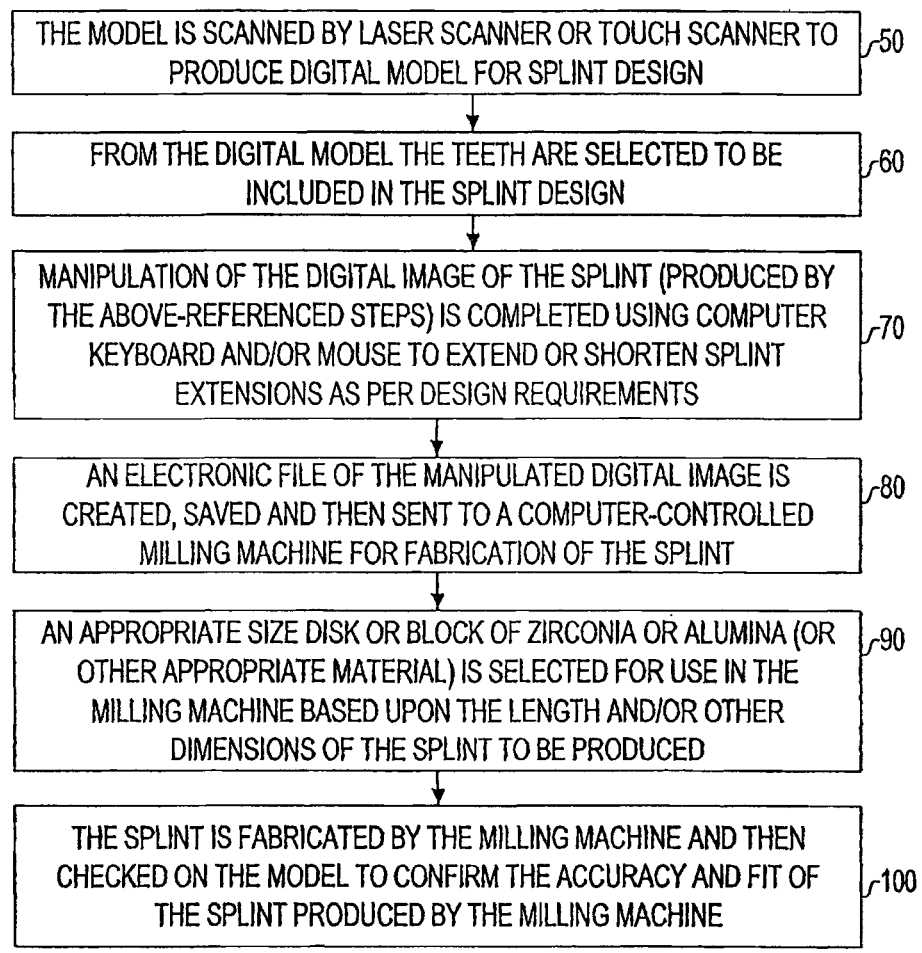
FIG. 6B is a flow chart containing detailed steps of the fabrication of the dental splint according to one embodiment of the present invention.

B. Fabrication of the Dental Splint:

Referring now to FIGS. 6A and 6B, the fabrication of the dental splint shall be described according to one or more embodiments of the present invention. Assuming that the dental professional has identified the tooth or teeth in need of stabilization or support, fabrication of the dental splint should begin by evaluating the patient's bite relationship with the teeth in the corresponding dental arch. In other words, the first step of preparing the dental splint fabrication 10 requires that a dental professional examine clinically a patient's dental arch. As known in the art, in certain patients (such as those with teeth in the maxillary arch requiring stabilization) it may be necessary to prepare or reduce the lingual fossa or cingulum areas prior to fabrication of the splint by procedures well known in the art. For example, in circumstances where the patient's arch exhibits a significant overbite or limited to no overjet. The mandibular arch would rarely require alteration unless the need for reduction of overlapping teeth is apparent or such teeth are problematic.

Subsequently, the next steps in preparing for the fabrication of the dental splint disclosed in FIG. 6A's flow chart involve creating a representative model of the patient's dental arch. One well-known method of creating a representative model involves the use of impression trays. In this method, the dental practitioner selects impression trays with a size appropriate to a patient's mouth 20, then fills the tray with any of the customary substances such as alginate or another collid substance, and lets the selected substance harden in the patient' mouth. It should be noted that taking impressions of the arch for splint fabrication can include at least two methods. First, the use of impression trays with an impression material that can be poured more than once is preferable and is recommended (e.g., polyether, polyvinyl-siloxane or alginate substitutes). Alternatively fabrication modeling may utilize a commercially available digital camera and scanning equipment along with accompanying software (e.g., Cadent Software) to take a digital impression of the patient's dental arch 30. Subsequent to hardening, the impression is used to fabricate an in-office model made of plaster or dental stone 40. Now the dental professional has an object that replicates the relevant dental arch. Next, as shown in FIG. 6B's flow chart, a commercially available scanning device is employed that produces digital data regarding three dimensional objects (often called a 3D scanner) to scan the model of the dental arch 50. An alternative embodiment of the present invention employs one of the various commercially available scanners of either the "touch scanner" variety or the "laser scanner" variety 30B. An example of a scanner that can be used to perform such functions include the CEREC Connect.RTM. scanner distributed by Sirona.

The information obtained from that scanning process is then transferred to a computer that is loaded with CAD/CAM software (typically proprietary) and designed to work with the particular scanning device used as well as the computer-controlled milling machine (discussed below) that will mill the dental splint from a block of material.

Yet another alternative embodiment of the present invention employs a 3D scanning device which incorporates computer software for generating a virtual model. For example, the inLab 3D® Scanner (also distributed by Sirona). Further, yet another embodiment of the present invention employs a scanner used to create digital impressions, such as Itero® from Cadent, Inc., which creates a virtual impression and model which can later be sent to the laboratory for dental splint fabrication.

The next step in fabricating a dental splint according to one or more embodiments of the present invention requires that the dental professional or lab technician select the teeth to be included in the dental splint design 60 from the representative model as shown in FIG. 6B' flow chart. Thereafter, manual adjustments of the digitally-generated image 70 would be performed. These adjustments can be performed through use of a mouse, keyboard or touch screen inputs to a monitor connected to the computer which allows the dental professional or technician to alter the dimensions of the digitally-generated image by drawing lines and/or placing markers (which then draw lines) on or near the extant computer-generated image to indicate the manner in which its dimensions are being revised as well known in the art.

Fabricating a dental splint according to one or more of the embodiments of the present invention involves several manual adjustments to the above-referenced computer-generated image. For example, the dental professional or technician will have to specify the number of teeth to be covered by the appliance (FIG. 6B, ref. 60) which correspond to the width (i.e., the horizontal length of the appliance in its installed position) of the appliance. In setting the length, the dental professional or technician also would have to determine the extent to which the appliance will span the first and last teeth in the section of the arch covered by the appliance. In one embodiment of the invention the entire widths of the first and last teeth are covered.

Also, the dental professional or technician (in the course of fabricating a dental splint according to one or more embodiment of the present invention) will have to make manual adjustments with respect to the height (i.e., the vertical dimensions) of the appliance in its installed position. In setting the height of the appliance, the dental professional or technician must consider the dimensions of each individual tooth in the arch that will be covered by the appliance. In one embodiment of the present invention, the height of the appliance is adjusted with respect to each individual tooth covered so that the appliance is approximately 1-4 mm from the biting edge of the tooth and approximately 1 mm above the portion of the gum that protrudes between that tooth and its adjacent tooth. This adjustment is intended to leave sufficient space interproximally (between the teeth) just above and below the gum line so that the patient can floss the area between the appliance and gingival, typically with the help of a floss threader.

Regarding the thickness of the dental splint, according to one embodiment of the present invention that dimension (at least initially) may be determined by the standard settings on the computer-controlled milling machine used to produce the dental splint (if such a milling machine is used). As known in the art, some computer-controlled milling machines are ordinarily set to produce appliances such as the dental splint described herein at a thickness of 0.4 mm while others may be set to produce appliances at a thickness of 0.7 mm. The thickness of the dental splint should be distinguished from the length of the dental splint (which is determined by the length of the arch of teeth involved) and the height of the splint (which can vary along the length of the splint and which depends in part upon the height of the particular teeth involved). One embodiment of the present invention provides that the dental splint described herein can be fabricated at a range of thicknesses from and including 0.3 mm up to and including 1.5 mm, depending upon the location of the dental splint in the mouth and the particular purpose or purposes to which the dental splint would be put.

An additional manipulation of the dental splint, according to one embodiment of the present invention includes providing beveled edges for the appliance. In other words, if the dental splint were produced at a uniform thickness, the resulting dental splint would be uncomfortable for the patient (i.e., upper and lower edges jutting out from the teeth to which they are attached). To avoid this problem, the upper and lower edges of the appliance are beveled. In some proprietary CAD/CAM software and milling machines known in the art the control software automatically creates bevels which involve thinning or rounding the edges of the material used to make the splint at the margins where the material meets the tooth. Were it not for that automatic beveling feature, the splint could, of course, cause irritation to the patient's tongue and otherwise prove uncomfortable. Although the user ordinarily should not have to bevel or thin the splint in those areas due to the automatic beveling feature of the CAD/CAM software, in the event that a particular CAD/CAM program does not automatically apply such bevels to the splint, or in the event that a different degree or type of bevel than the one automatically determined by a CAD/CAM program is desired, the user can employ the above-referenced mouse, keyboard or touch screen inputs to a monitor to control a bevel or taper to the upper and lower edges of the 3D image of the appliance so that those edges form a smooth joint with the surface of the tooth. The dental professional or technician can manipulate the 3D image of the appliance to achieve that result by eye. When working with a CAD/CAM program that does not automatically apply the above-referenced 30 degree bevels, the dental professional or technician can, as a general guideline, adjust the 3D image of the splint to achieve a bevel of approximately 30 degrees on the edges of the appliance. In the event the splint described herein is not fabricated on a computer-controlled milling machine, the edges of the splint can be beveled by traditional grinding methods.

Once the dental professional or technician has finished making the above-described width, height and thickness adjustments to the image of the dental splint, the digital information from the computer is saved to a file and then transferred to a milling machine 80 as show in FIG. 6B. According to one embodiment of the present invention, the milling machine is directed to mill or fabricates a desired dental splint from zirconia, alumina or another suitable material. For example, various scanner and CAD/CAM software programs described above allow this data to be transferred directly to the milling machine. An example of such a milling machine is the inLab® available from Sirona. Thereafter, the milling or fabrication of the dental splint can be produced immediately in the dental practitioner's office (if the costly machine is available), or the digital information is generally transferred to a remotely-located milling machine over the Internet. Although transmission of such data over the Internet is the customary method of transmission, other commonplace methods for supplying the computer-controlled milling machine with the data can be used (e.g., transmission over telephone lines, transfer of data by CD-ROM, or flash drive, etc.).

Before actually milling the dental splint, however, the material to be used must be selected (e.g., zirconia, alumina or other suitable material) and the dimensions of the block or disk from which the splint will be milled must be specified (FIG. 6B, ref. 90). Selection of the material to fabricate a rigid force transfer component involves consideration of several issues. Zirconia (which is commercially available for use in milling machines in blocks or round disks of various dimensions) can be used to manufacture essentially any dental splint that be created through the process described herein. As known in the art, the dimensions of the block or disk of zirconia (or alumina, other suitable material) used depends in part upon the particular milling machine that is used to fabricate the splint in that certain milling machines are designed to work with blocks of particular dimensions.

According to one embodiment of the present invention, the selection of the dimensions of the block or disk is determined by the following rubric: the material must be large enough so that the desired dental splint can be milled in one piece from it. For example, a dental splint that is to be used with respect to an arch involving many teeth might have to be milled from a relatively large disk or block of zirconia. In one embodiment of the present invention, such a dental splint involving many teeth would require selection of a material with the following dimensions: 30 mm in height and 60 mm in diameter. Also, in selecting the size of the block or disk to be used, according to one embodiment of the invention, one must be mindful of the Curve of Spee (also called von Spee's curve or Spee's curvature) which necessitates use of thicker blocks or disks when fabricating a splint that will be bonded to an arch including anterior teeth and back teeth such as molars or wisdom teeth. In alternative embodiment, selecting the dimensions of the block or disk of material to be used, involves using smaller block sizes when the splint to be fabricated permits it. For example, a relatively small block or disk can be used if the dental splint will be bonded to only a few anterior teeth. Most commercially available computer-controlled milling machines have milling or grinding apparatuses that employ diamond burs. In the event that no commercially available computer controlled milling machine works with blocks or disks of the dimensions needed to produce the desired splint, the splint can be produced using more traditional milling methods that do not involve use of such computer controlled machinery as known in the art.

In selecting the material to be used to fabricate a splint as described herein, factors such as the strength, rigidity, brittleness, durability and its ability to bond to the teeth also should be considered. According to one embodiment of the present invention, zirconia can be used to produce any dental splint described herein. An alternative embodiment of the present invention utilizes alumina to produce dental splints described herein. However, zirconia (which is a stronger material than alumnia), is the preferred embodiment when producing a dental splint for an arch involving a large number of teeth As well as other splints that are expected to be subjected to greater stresses than splints involving a few teeth. As mentioned above, since the dental splint described herein is a new invention, clinical data developed through use of various materials to make the splint described herein will undoubtedly provide guidance regarding the best material to use in various circumstances. Furthermore, since new dental materials with different properties and characteristics are always being brought to market, those new materials can be used to fabricate the splint described herein if they meet or exceed the desirable characteristics of zirconia or alumina.

Another factor considered when selecting the appropriate material for the fabrication of the dental splint according to one or more embodiments of the present invention is color selection. A dental professional or technician, in order to produce a rigid force transfer component which is substantially non-visible facially, must specify a color of that material from the several different ones commercially available. Color selection generally involves matching the color of the tooth surfaces to which the appliance will be bonded, but other color choices can be made.

Once the material and its thickness have been selected and loaded into the milling machine, the machine mills the appliance based upon the above-referenced digital information regarding the dimensions of the dental splint. According to one or more embodiments of the present invention, a dental professional or technician next checks the fit and contours of the dental splint against either the dental stone model or the digitally-fabricated model. (FIG. 6B, ref. 100). That is, although the milling process performed by such machines are generally highly accurate, a dental professional or technician should check the fit and contours of the splint against either the dental stone model or the digitally-fabricated model. As such a dental professional or technician may make adjustments to the appliance by traditional methods known in the art such as grinding (for example, with diamond grit burs under copious water) in order to make the appliance conform more closely to the dimensions called for by the impression or digitally fabricated model described above. Once the dental professional or technician has performed any such repairs or adjustments, the appliance is then delivered to the dentist's office.

Although, as explained above, the dental splint according to one or more embodiments of the invention can be manufactured through use of modern techniques involving scanners, computers, CAD/CAM software and a computer-controlled milling machine, the dental splint described herein can be produced through use of more traditional dental techniques. For example, instead of using the equipment described above in this paragraph, a user can manufacture the splint by: 1) taking an alginate or wax impression of the relevant dental arch or arches, 2) making (or having a dental laboratory) fabricate an in-office lab model made of plaster or dental laboratory stone, 3) determining the dimensions of the dental splint with information supplied by the dentist regarding the length, width and height of the splint and the particular teeth to which the splint will be bonded, 4) fabricating a model of the splint from wax, acrylic or any similar dental materials, 5) sending that model of the splint to a dental laboratory that can manufacture the actual splint out of zirconia, alumina or other suitable material through use of the above-referenced CAD/CAM technology. Although it is possible to fabricate the dental splint with such traditional methods, use of the more modern techniques is more expeditious and requires less work by laboratory personnel and dental professionals to produce the final version of the dental splint so as it can be successfully installed in the patient.

Figure 6C:
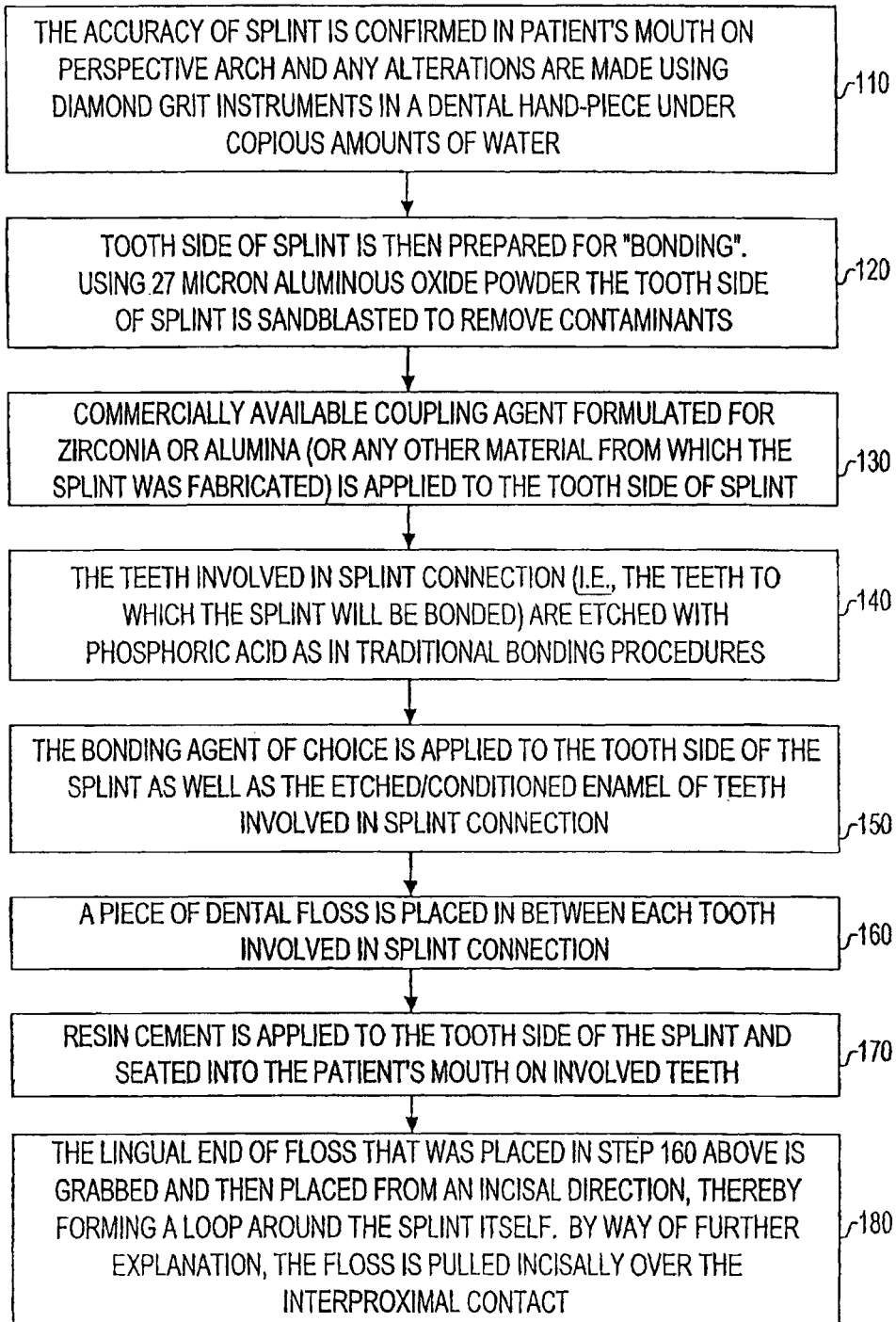
FIG. 6C is the first half of a flow chart containing the steps employed in clinical insertion of the splint to one embodiment of the present invention.

C. The Clinical Process—Installation of the Splint:

Referring now to FIGS. 6C and 6D, the method for clinically inserting the dental splint into a patient's mouth according to one embodiment of the invention shall now be described. As known in the art, a preliminary "try in" of the appliance in the patient's mount is employed by the dental professional to verify fit and contour. Any adjustments at this stage is employed to permit passive seating of the dental splint extra-orally with high speed drills with diamond burs under copious amount of water (FIG. 6C, ref 110). The bonded side (FIG. 1, ref 2b) (i.e., tooth-surface side) of the dental splint is then "sandblasted" with 27 micron aluminous oxide to remove contaminants (FIG. 6C, ref. 120). Then, a coupling agent is applied to the bonded side 2b (FIG. 1) of the dental splint. Since coupling agents are typically intended for use only with certain materials, an appropriate coupling agent is one that is intended to be used with the material from which the splint is fabricated (FIG. 6C, ref. 130).

Subsequently, the teeth involved in the "splint connection" (i.e., the teeth to which the splint will be bonded) are etched with phosphoric acid as in traditional bonding procedures as known in the art (FIG. 6C, ref. 140). According to one embodiment of the invention, a commercially-available bonding agent is applied to the bonded side 2B of the dental splint, as well as to the etched or conditioned enamel of the teeth involved in the splint connection (FIG. 6C, ref. 150).

According to one embodiment of the present invention, a technique known in the art as the "looped floss" technique is employed to seat the dental splint and minimize resin thickness. Referring now to FIG. 3, a piece of dental floss 4 is placed inter-proximally between each tooth 3 that will be connected to the splint (FIG. 6C, ref. 160). As explained further below, this will facilitate placement of the splint (that is, it will help the dental professional position and pull the splint into place), as well as simplify the post-bonding cleanup of excess material. Resin cement (light-cured, self-cured or dual-cured resin cement can be used) is then applied to the bonded side 2b of the surface of the splint and placed intra-orally onto the teeth (FIG. 6C, ref. 170).

As illustrated in FIG. 4, several loops of floss 4a are installed inter-proximally. By pulling the lingual part of each loop of floss 4a (inter-proximally placed piece of floss) and reinserting the floss inter-proximally from the incisal direction, a loop is created around the dental splint 1 to enable the dentist to apply a comfortable level of force to the splint by pulling the floss facially to insure intimate contact between the splint and the teeth and to minimize resin thickness (FIG. 6D, refs. 180 and 190).

While applying consistent pressure with the dental floss loops from a facial direction, and prior to the curing of the resin, any excess resin is removed with gauze, Q-tips, disposable bonding brushes or a combination of the above (FIG. 6D, ref 200). As known in the art, a light-cured resin cement can be employed whereby a curing light is be applied to initiate hardening of the resin cement. Alternatively, a self-cured resin cement is employed, together with pressure applied by way of the floss, to maintain the appliance in place until the resin curing is complete. (FIG. 6D, ref 210). Inter-oral evaluation is then preformed and any residual cement is removed from the tooth or teeth involved as well as the gum tissue areas 220.

According to one embodiment of the present invention, a technique known in the art as the "looped floss" technique is employed to seat the dental splint and minimize resin thickness. Referring now to FIG. 3, a piece of dental floss 4 is placed inter-proximally between each tooth 3 and above the gum 5 that will be connected to the splint (FIG. 6C, ref 160). As explained further below, this will facilitate placement of the splint (that is, it will help the dental professional position and pull the splint into place), as well as simplify the post-bonding cleanup of excess material. Resin cement (light-cured, self-cured or dual-cured resin cement can be used) is then applied to the bonded side 2b of the surface of the splint and placed intra-orally onto the teeth (FIG. 6C, ref. 170).

Next, occlusal evaluation is performed and any premature contacts are reduced accordingly. (This is typically done with diamond grit instruments under a copious water spray). Careful inspection of the now-bonded dental splint is performed to insure all excess resin has been removed. (FIG. 6D, ref. 240).

Once installed, the dental splint ordinarily should be evaluated at regular intervals such as the patient's usual six month checkups or perhaps more frequently if indicated. (e.g., such as in applications pertaining to traumatic injuries). Splint maintenance and hygiene procedures (such as use of floss threaders) are then discussed with the patient as are arrangements for the above-referenced periodic evaluations. (FIG. 6D, ref. 250).

In accordance with the present invention, there is provided a dental splint device for stabilizing mobile or unstable human or animal teeth, a procedure for fabricating such a splint and a splinting procedure (i.e., a procedure for installing the splint). Furthermore, with respect to the above-referenced device, the present invention relates to a rigid, one-piece extra-coronal (that is, external to the natural tooth) dental splint made of commercially available dental zirconia, or dental alumina (or a material with properties similar to either of those substances), that is custom made to fit the contours of teeth to which the dental splint will be bonded (i.e., in one embodiment, several teeth all of which require support and in another embodiment, a row of teeth in which one or more of the end teeth are firmly anchored supporting teeth and the teeth in the middle of the dental splint are teeth requiring support) on the lingual aspect of the dental arch (i.e., the inner dental arch) and that is adhered to the patient's inner dental arch with a thin layer of composite or bonding material. Generally speaking, one of the dental splint's basic purposes is the retention of teeth in a desired position in the mouth. More specifically, the device is intended to maintain and/or retain the position of a series of upper or lower teeth within the same arch. The dental splint addressed herein can be categorized as a permanent or semi-permanent dental appliance in that once installed it can be removed only by a dental professional.

As explained herein, the dental splint is diverse in its applications in that it can be used in a variety of circumstances and to address a number of different dental conditions and problems. For example, the splint can be used for "fixed" orthodontic stabilization to prevent orthodontic relapse in both the maxillary and mandibular arches. The splint also can be used for periodontic stabilization of teeth that have become mobile due to the loss of supporting bone (i.e., loss of bone that is normally adjacent to the roots of teeth). Although this particular use of the splint would probably most often be employed with respect to anterior teeth, the dental splint also can be used for this purpose with respect to teeth located elsewhere in the mouth. An additional use of the present invention includes the splinting of one or more teeth which exhibit mobility due to traumatic injury. Furthermore, the dental splint also can be used with respect to one or more avulsed teeth which could be reinserted and then stabilized and supported by being splinted to adjacent, non-avulsed teeth. The present invention also can be used to splint teeth that have very short roots and/or teeth that have experienced "root blunting" due to orthodontic tooth movement or other causes. Although the present invention's use with respect to teeth with short roots or root blunting would primarily involve the anterior teeth, the splint also could be used for other teeth with those problems.

Regarding the various uses to which the present invention could be put, it should be noted that although a number of those uses involve splinting one or more teeth that are in need of stabilization or support to one or more other teeth not in need of support (i.e., firmly anchored or firmly rooted teeth which could be called "supporting teeth"), the present splint also can be employed with respect to a series of teeth all of which need support. That is, although the splint described herein often would be applied to series or arch of teeth that included one or more teeth needing support as well as one or more teeth providing support, the splint also can be used with respect to a series of two or more teeth both or of which all needing support. Such a use of the splint is beneficial in that splinting such a series of teeth together provides support and stabilization to each and all of them that they would not individually or collectively have in the absence of the splint. In other words, the dental splint once installed in a patient's mouth becomes a rigid and substantially acts as a force transfer component customized to the dentition of a patient's dental arch.

Moreover, the dental splint described herein can be bonded to a group of teeth which are firmly rooted to prevent orthodontic relapse. For example, a well known by Orthodontic specialists, patent's sometime fail to wear dental retainers as instructed by their dentist which results in movement of previously treated malaligned teeth. Similar relapse can occur after removal of braces which corrected malaligned teeth. Accordingly, by installing the present invention dental splint on a group of the firmly rooted teeth (subject to orthodontic treatment) can prevent orthodontic relapse.

What is claimed is:

1. A method of fabricating a one-piece extracoronal component for stabilizing mobile or unstable teeth, comprising the steps of:
   examining a patient's dental arch to determine if lingual reduction is required;
   creating a representative model of the patient's dental arch;
   manipulating said representative model to select a group of teeth to be included in the one-piece extracoronal component and to define the height and length of the one-piece extracoronal component customized to the dentition of a patient;
   fabricating said one-piece extracoronal component from zirconia;
   dry fitting the fabricated one-piece extracoronal component to confirm proper fit; and
   adhering the fabricated one-piece extracoronal component to only the mobile or unstable teeth,
   wherein said one-piece extracoronal component adheres to the lingual aspect of said mobile or unstable teeth, functions substantially as a force transfer component, so customized to the dentition of a patient's dental arch and appears substantially non-visible facially.

2. The method of claim 1, wherein the step of creating a representative model of the patient's dental arch further includes the steps of:
   selecting an impression tray appropriate to a patient's mouth;
   pouring an impression material in said selected impression tray;
   allowing said impression material to harden in the patient's mouth; and
   fabricating from plaster or dental stone said representative model.

3. The method of claim 1, wherein the step of creating a representative model of the patient's dental arch further includes the steps of:
   scanning a three dimensional representation of the patient's dental arch in order to obtain a three dimensional image of the patient's dental arch, wherein a commercially available scanning device is employed.

4. The method of claim 3, wherein the commercially available scanning device further incorporates computer software for generating a virtual model of a patient's dentition.

5. The method of claim 1, wherein the step of manipulating said representative model to select a group of teeth to be included in the one-piece extracoronal component and to define the height and length of a one-piece extracoronal component customized to the dentition of a patient further includes the steps of:
   adjusting a distance between a bite edge of each said tooth and the edge of the one-piece extracoronal component 1-4 mm from the bite edge and 1 mm above a gum between at least one tooth and an adjacent tooth to said tooth.

6. The method of claim 1, wherein the step of fabricating said one-piece extracoronal component further includes the steps of:
   milling said one-piece extracoronal component with a thickness of 0.4 mm.

7. The method of claim 1, wherein the step of fabricating said one-piece extracoronal component further includes the steps of:
   milling said one-piece extracoronal component with a thickness of 0.7 mm.

8. The method of claim 1, wherein the step of fabricating said one-piece extracoronal component further includes the steps of:
   milling said one-piece extracoronal component with a thickness of a range from and including 0.3 mm up to and including 1.5 m, adapted to the location of the one-piece extracoronal component in the mouth and the particular purpose or purposes of the one-piece extracoronal component.

9. The method of claim 1, wherein the step of fabricating said one-piece extracoronal component further includes the steps of:
   milling said one-piece extracoronal component to a consistent thickness or a variable thickness.

10. The method of claim 1, further including the step of:
    color matching said selected material to the patient's teeth.

11. The method of claim 1, wherein the one-piece extracoronal component is installed on a group of two teeth.

12. A method, comprising:
    fabricating a one-piece extracoronal zirconia component adapted for immobilizing or supporting a group of teeth subject to root blunting; and
    adhering the fabricated one-piece extracoronal zirconia component only to the group of teeth subject to root blunting,
    wherein said one-piece extracoronal zirconia component adheres to the lingual aspect of said teeth, functions substantially as a force transfer component, is customized to the dentition of a patient's dental arch, appears substantially non-visible facially and prevents orthodontic relapse.

* * * * *